United States Patent [19]

Hoeschele

[11] 4,287,187

[45] Sep. 1, 1981

[54] METHOD FOR TREATING TUMORS WITH CIS-DIAMMINEPLATINUM(II) ORTHOPHOSPHATE COMPLEXES

[75] Inventor: James D. Hoeschele, Oakridge, Tenn.

[73] Assignee: Engelhard Minerals & Chemicals Corporation, Iselin, N.J.

[21] Appl. No.: 106,436

[22] Filed: Dec. 26, 1979

Related U.S. Application Data

[62] Division of Ser. No. 17,994, Mar. 7, 1979.

[51] Int. Cl.³ .................... A61K 31/685; A61K 31/28
[52] U.S. Cl. ................................. 424/199; 424/287
[58] Field of Search ........................... 424/199, 287

[56] References Cited

U.S. PATENT DOCUMENTS 4,115,418  9/1978  Gale et al. ..................... 424/278

OTHER PUBLICATIONS

Rosenberg et al., Nature, vol. 222, 1969, pp. 385–386.
Cleare, Coordination Chemical Reviews, 12, (1974), pp. 349–405.
Cleare et al., Bioinorganic Chemistry, 2, 1973, pp. 187–210.
Gale et al., Cancer Treatment Reports, 61, 1977, pp. 1519–1525.

*Primary Examiner*—Jerome D. Goldberg

[57] ABSTRACT

Cis-diammineplatinum(II) orthophosphate complexes are prepared by reaction of diaquo-cis-diammineplatinum(II) salts with alkali metal orthophosphates. The resulting complexes possess pronounced activity against tumors in mice combined with low animal toxicity.

4 Claims, 2 Drawing Figures

METHOD FOR TREATING TUMORS WITH CIS-DIAMMINEPLATINUM(II) ORTHOPHOSPHATE COMPLEXES

This is a division of application Ser. No. 17,994, filed Mar. 7, 1979.

This invention is concerned with cis-diammineplatinum (II) phosphate complexes. More particularly, this invention is concerned with cis-diammineplatinum-(II) orthophosphate complexes. These complexes are characterized by pronounced activity against tumors in mice combined with low animal toxicity.

In this Specification the term "tumors" refers to experimentally-induced tumors such as S-180 ascites tumors and lymphocytic leukemia P-388 tumors.

BACKGROUND

Figure 2:
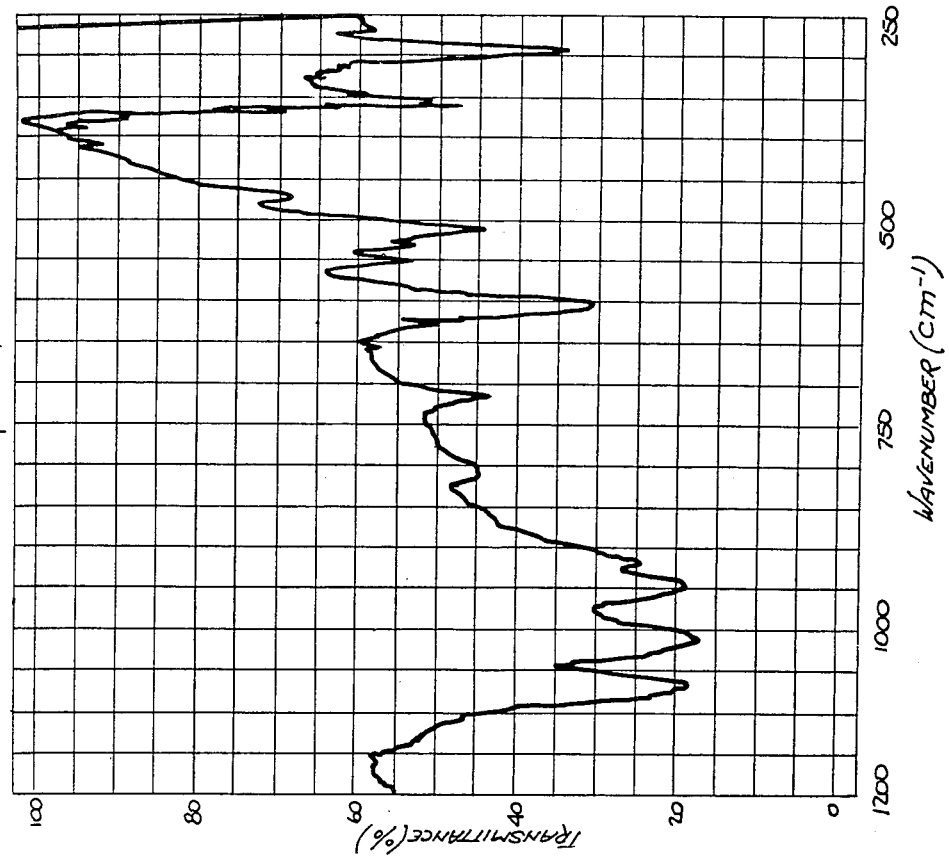
FIG. 2 shows the infra-red spectrum of the complex of Example 2.

Rosenberg et al reported the discovery that certain platinum coordination compounds are of interest as potential antitumor agents. (Rosenberg et al, "Platinum Compounds: A New Class of Potent Anti-Tumor Agents," Nature, Vol. 222 (Apr. 26, 1969), pp. 385–86). Since then, considerable effort has been expended to evaluate various classes of coordination complexes for similar activity. See, e.g. M. J. Cleare, "Transition Metal Complexes in Cancer Chemotherapy," Coordination Chemistry Reviews, 12 (1974), pp. 349–405. Cis-diammineplatinum pyrophosphate complexes of the empirical formula $\{Pt(NH_3)_2\}_2P_2O_7$ have been reported; however, they have only marginal activity. (Cleare et al, "Studies of the Antitumor Activity of Group VIII Transition Metal Complexes, Part I, Platinum(II) Complexes," Bioinorganic Chemistry, 2, pp. 187–210 (1973) at p. 199).

A blue, water soluble, orthophosphate complex of 1,2-diaminocyclohexaneplatinum(II) containing 45.85% platinum (Pt) has been reported to show anti-tumor activity (G. R. Gale et al, "Preparation and Antitumor Evaluation of Water-Soluble Derivatives of Dichloro-1,2-diaminocyclohexane platinum(II)", Cancer Treatment Reports, 61, pp. 1519–25 (1977)).

SUMMARY OF THE INVENTION

In accordance with the present invention, there is provided a novel class of cis-diammineplatinum(II) orthophosphate complexes which, unlike the known pyrophosphate complexes, have exhibited pronounced anti-tumor activity in mice. In addition, they have low mammalian toxicity. As a consequence, the complexes of this invention have a favorable therapeutic index.

This invention is concerned with a class of platinum-(II) complexes which comprise the cis-diammine moiety which may be represented by the general formula:

cis-$\{Pt(NH_3)_2\}$ and an orthophosphate moiety which may be represented by the general formula:

$$H_{(2-n)}PO_4{}^{-(1+n)}$$

wherein n is 0 or 1 and wherein the atomic ratio of phosphorus to platinum is about 0.5 to 1 or about 1 to 1. Said complexes may be either hydrated or anhydrous.

The complexes of this invention are prepared by reacting a diaquodiammineplatinum(II) salt with an orthophosphate salt in an aqueous medium. The diaquodiammineplatinum(II) salt is represented by the formula:

$$[Pt(NH_3)_2(H_2O)_2]^{+2}(X^{-(2-u)})_{1+u}$$

wherein X is an inorganic anion and u is 0 or 1. Suitable anions are those which are stable in acid media and which do not effect pH; they include sulfate, nitrate, and perchlorate, although nitrate is preferred. Anions having a greater complexing ability than water or orthophosphate, such as chloride, iodide and bromide are not suitable.

The diaquo salt is formed by the stoichiometric reaction of cis-dichlorodiammineplatinum(II) with a silver salt, preferably silver nitrate, in an aqueous medium at room temperature. Although room temperature is preferred for the reaction, higher or lower temperatures may be employed, e.g., from about 0° C. to about 50° C. The diaquo salt is unstable in solution, but may be converted to stable solid cis-$[Pt(NH_3)_2(OH)]_2(X)_2$ by reaction with one gram mole of base per gram atom of platinum. The dimeric complex may be reconverted to monomer with acid or used directly in the preparation of phosphate compounds.

The orthophosphate salts which are employed are water soluble monohydric or dihydric salts, preferably alkali metal orthophosphate salts such as sodium dihydrogen phosphate or disodium hydrogen phosphate.

Depending upon both the phosphorus/platinum ratio of the reaction mixture and its initial pH, either a yellow complex or a gray or blue complex is formed. The yellow complex is believed to have the empirical formula cis-$[Pt(NH_3)_2(OH)]_2(H_2PO_4)_2$, while the gray and blue complexes are believed to be oligomeric or polymeric complexes containing cis-$Pt(NH_3)_2$ moieties and phosphate moieties, possibly as bridging groups.

The initial pH may be controlled by choice of the phosphate starting material (for example, whether $Na_2HPO_4$ or $NaH_2PO_4$ is chosen), and by the use of base if desired.

The yellow species may be formed at ambient temperature (although higher temperatures, up to 70° C., may be used) by either of two reactions illustrated by the following equations:

(1) cis-$[Pt(NH_3)_2(H_2O)_2](X)_2$ + $Na_2HPO_4 \longrightarrow$ $[Pt(NH_3)_2(OH)]_2(H_2PO_4)_2$ (2) cis-$[Pt(NH_3)_2(OH)]_2(X)_2$ + $2NaH_2PO_4 \longrightarrow$ The cis-$[Pt(NH_3)_2(OH)]_2(H_2PO_4)_2$ is a slightly soluble, pale yellow solid. In reaction (1) the complex precipitates while $Na_2HPO_4$ is being added to the cis-$[Pt(NH_3)_2(H_2O)_2](X)_2$ solution; the pH at the time of precipitation is about 4.5 to 5.3. Reaction (2) consists of a recrystallization of cis-$[Pt(NH_3)_2OH]_2(X)_2$ from a solution containing $NaH_2PO_4$ at a pH of about 5. It is a less desirable method due to contamination of product with starting material, since both are relatively insoluble solids. A ratio of phosphorus to platinum of about 1:1 in the reaction mixture is preferred, although higher phosphorous/platinum ratios may be used if desired.

Increasing the effective base content of the reaction mixture by at least one molar equivalent of base per gram atom of platinum, in order to achieve a pH of 5–7, results in formation, over a more extended time period, about 15 hours or more, of the second phosphate complex. This complex may be prepared by one of three reactions as illustrated:

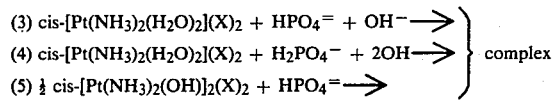

Analysis of the reaction product indicates that the complex contains intact cis-$Pt(NH_3)_2$ units, has coordinated orthophosphate moieties, and has a phosphorous/platinum ratio of approximately 0.5:1. The color of the complex, which is completely insoluble in water, is gray or blue/gray. The complex is believed to be oligomeric or polymeric.

Starting mixtures, as shown in equations (3)–(5), that are approximately equal molar in phosphate and platinum with an initial pH of about 7.25 yield an optimum reaction time of 24 hours. However, somewhat lower initial pH's may be used, provided that a phosphorous/platinum ratio of about 1:1 is maintained. Reaction mixtures with initial pH's outside the range of about 5 to about 7.25, and which have phosphorous/platinum ratios which are not about 1:1 yield other distinct complexes.

The complexes of this invention are of particular utility in tumor chemotherapy, having been found to be active against sarcoma 180 ascites in mice. The complex is administered intraperitoneally as an aqueous solution in a generally known manner or, in cases where the complex has low solubility in water, as a slurry with Klucel (hydroxypropyl cellulose) or other suitable suspending agent. The solution or slurry may contain other components, such as physiologically acceptable salts, other medicaments, etc.

The dosage level required for anti-tumor activity is not narrowly critical, and indeed it is a feature of the complexes of this invention that, because of their relatively low toxicity, they may be administered over a wide dosage range. In mice having experimentally induced tumors, effective dosages as low as 2.5 mg/kg of body weight, or even lower, up to 30 mg/kg have been observed for the yellow complex. The oligomeric blue-gray complexes are somewhat less active, having demonstrated anti-tumor activity against experimentally-induced tumors in mice over a range of from about 20 mg/kg to about 80 mg/kg. The increased dosage level and range of activity are believed due to the extreme insolubility of these complexes. In effect, they provide a solid reservoir from which the active agent is slowly released.

The activity of the complexes of this invention also appears to be affected by the injection medium employed. For example, administration of the yellow complex in phosphate buffer having a pH of about 5 appears to increase the toxic dose over that observed when the same complex is administered in water.

The following examples are illustrative of the present invention.

EXAMPLE 1

Synthesis of Cis-$[Pt(NH_3)_2(OH)]_2(H_2PO_4)_2$

A 40-milliliter portion of 1 M disodium hydrogen phosphate (0.04 moles) was added dropwise to 100 milliliters of 0.4 M diaquo-cis-diammineplatinum(II) nitrate, cis-$[Pt(NH_3)_2(H_2O)_2]$-$(NO_3)_2$, over a 5-minute period at ambient temperature. Precipitation of a yellow solid occurred at a pH of about 4.5 to 5.3. After stirring for 5 minutes, the yellow precipitate was filtered from the reaction mixture and washed with water and ethanol. After drying briefly in a vacuum desiccator, there was recovered 10.9 grams (72.0% yield) of hydrated cis-diammineplatinum(II) orthophosphate, cis-$[Pt(NH_3)_2(OH)]_2(H_2PO_4)_2.4H_2O$.

Analysis: cis-$[Pt(NH_3)_2(OH)]_2(H_2PO_4)_2.4H_2O$. Calculated: H, 3.69%; N, 7.37%; P, 8.15%; Pt, 51.32%. Found: H, 3.46%; N, 7.38%; P, 8.05%; Pt, 51.54%.

Prolonged drying in a vacuum desiccator will result in the loss of the water of hydration.

Analysis: $[Pt(NH_3)_2(OH)]_2(H_2PO_4)_2$. Calculated: H, 2.64%; N, 8.16%; P, 9.02%; Pt, 56.03%. Found: H, 2.77%; N, 8.32%; P, 9.47%; Pt, 58.73%.

The hydrate was unstable in air, and will turn blue after about 24 hours exposure to ambient air. This reaction was more rapid in the presence of added moisture. The dried product was stable for at least 2 months when stored under vacuum.

Figure 1:
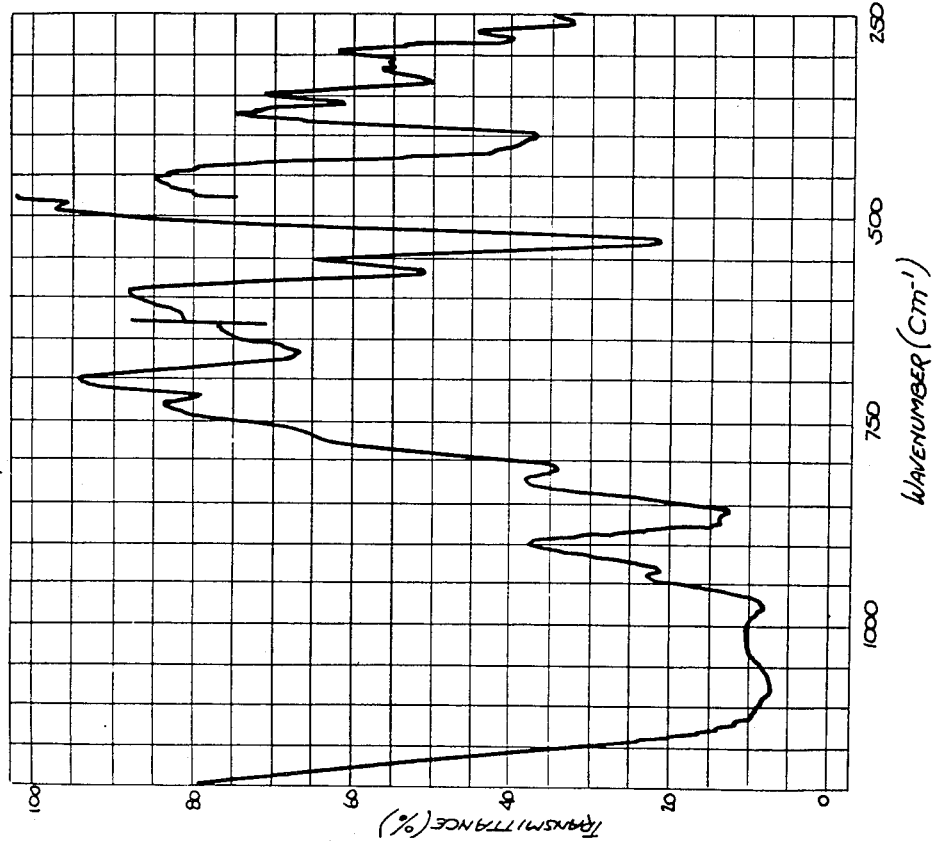
FIG. 1 shows the infra-red spectrum of the complex of Example 1.

The assigned structure was confirmed by infra-red analysis, the spectrum of which is reproduced in FIG. 1. The absorption bands at 480, 525 and 564 cm$^{-1}$ are similar to those previously reported and assigned to $\nu_{Pt-N}$ and $\nu_{Pt-O}$ for cis-$[Pt(NH_3)_2(OH)]_2(NO_3)_2$ and cis-$[Pt(NH_3)_2(OH)]_2(ClO_4)_2$.

A $5.17 \times 10^{-4}$ M aqueous solution of the product had a specific conductance (K) of 76.7 mho cm$^{-1}$ and molar conductance ($\Lambda$) of 148 mho cm$^2$ mole$^{-1}$, as compared with K of 132.8 mho cm$^{-1}$ and $\Lambda$ of 254 mho cm$^2$ mole$^{-1}$ for a $5.22 \times 10^{-4}$ molar solution of $[Pt(NH_3)_2(OH)]_2(NO_3)_2$.

EXAMPLE 2

Synthesis of cis-$\{Pt(NH_3)_2\}_2(HPO_4)(OH)_2(H_2O)$ Complex

A 100-ml portion of a 0.4 M aqueous solution of cis-$[Pt(NH_3)_2(H_2O)_2](NO_3)_2$ was diluted with water to 1300 ml, and a solution of 4.8 grams of sodium dihydrogen phosphate in 200 ml of water was added. The pH of the solution was adjusted to 7.0 with 35 ml of 2 M sodium hydroxide, and the resulting solution was stirred for 24 hours at room temperature and under an oxygen atmosphere. A blue-gray solid that had formed was allowed to settle and the supernatant liquid was decanted. The remaining slurry was transferred to centrifuge tubes and the solid was washed by alternate centrifugation and resuspension in water. The resulting aqueous suspension was frozen, thawed, filtered and washed with water and alcohol. After vacuum drying, there were obtained 6.98 grams (yield 56.7% based on Pt) of a blue-gray solid having the empirical formula cis-$\{Pt(NH_3)_2\}_2(HPO_4)(OH)_2(H_2O)$.

Analysis: $\{Pt(NH_3)_2\}_2(HPO_4)(OH)_2(H_2O)$. Calculated: C, 0.00%; H, 2.83%; N, 9.24%; P, 5.11%; Pt, 64.35%. Found: C, 0.35%; H, 2.99%; N, 9.12%; P, 5.09%; Pt, 63.36%.

A second crop of solid product was obtained by stirring the original supernatant and the combined centrifugates for an additional 96 hours under an oxygen atmosphere.

The infra-red spectrum of this product is reproduced as FIG. 2. In comparison with the spectrum of FIG. 1, it contained sharper, more numerous phosphate bands in the region of 950–1080 cm$^{-1}$, which indicated that the product contained coordinated, possibly bridging phosphate moieties.

The product was totally insoluble in water at ambient conditions. It reacted readily with warm 2 M hydrochloric acid, and on cooling it formed cis-[Pt(NH$_3$)$_2$Cl$_2$], thereby indicating that the cis-Pt(NH$_3$)$_2$ moiety was present in the product. The supernatant gave a positive test for phosphate with ammonium molybdate.

EXAMPLE 3

Synthesis of cis-[Pt(NH$_3$)$_2$(phosphate)$_x$] Complex

A 7.05-gram portion of disodium hydrogen phosphate was dissolved in 50 ml of 1 M NaOH, and the solution was diluted with water to 150 ml. A 117-ml portion of 0.42 M cis-[Pt(NH$_3$)$_2$(H$_2$O)$_2$](NO$_3$)$_2$ was then added, and the mixture (pH=7.25) was warmed briefly to 50° C. After cooling, the flask was stoppered and the reaction mixture was stirred for 24 hours at room temperature. The gray solid which had formed was filtered, washed with water and ethanol, and dried in a vacuum. There were obtained 14.6 grams (94.4% yield based on Pt) of gray solid product similar to that produced in the experiment of Example 2. Found: Pt, 62.84%.

EXAMPLE 4

Evaluation of the Anti-Tumor Activity of the Complex of Example 1 in the Mouse S180a Tumor System The cis-diammineplatinum(II) orthophosphate complex of Example 1 was tested for anti-tumor activity against S180 ascites in female Swiss white mice by the following procedure:

CFW mice, averaging 20 grams, were immediately inspected, weighed, and then placed in newly prepared cages (6 mice/cage or 1 set). On day 0 the mice were inoculated with 0.2 ml of a freshly prepared saline suspension (0.15 M NaCl) containing 1×10$^7$ tumor cells/ml or a total of 2×10$^6$ cells. This inoculum was freshly prepared using "transfer" mice which had been injected with tumor cells the previous week, and was the end-product of a series of steps which involved (1) the removal of the cells from the peritoneal cavity of the sacrificed transfer mouse, (2) alternate centrifugation-washing (2–3 times with cold saline), to remove occasional blood and other undesirable components, and (3) dilution (1:3) of the packed cell volume with saline (the final centrifugation being carried out at 1000 rpm for two minutes). A cell count was made (in duplicate) on a 100-fold dilution of this 1:3 suspension (nominally 5×10$^7$ cells/ml) by means of a hemacytometer counting chamber and a microscope and in most cases by means of a Coulter Counter. A final dilution to 1×10$^7$ cells/ml was made based on the averaged count (normally about 500–600 cells were counted to obtain reliable statistics when the hemacytometer method was employed). On day 1, solutions of the test compounds were prepared and the mice injected, with each mouse of a set of six mice being injected with the same test compound at the same dosage level. The doses were based on the average weight of the animals (cage weights).

Also, on day 1 two types of controls were employed: (1) Normal (1 set): 0.5 ml of the carrier used for the test compound; (2) Positive Control (1 set): cis-dichlorodiammineplatinum(II), a known anti-tumor agent, used at 7 or 8 mg/kg as a check on the response of the biological test system.

The effectiveness of a compound was measured in terms of the % increase in life span (%ILS) of the test animals relative to the normal controls (calculated from the day of tumor inoculation (day 0)). In order to standardize the test data and permit inter-comparisons to be made, the day of evaluation was arbitrarily taken as that day corresponding to twice the mean lifespan (or average day of death) of the normal controls. This set a practical upper limit of 100% on the %ILS attainable. For purposes of calculation, survivors on the day of evaluation were considered to have died on that day. The %ILS was formulated as:

$$\%ILS = \left( \frac{\text{mean-life span of test mice}}{\text{mean-life span of control mice}} - 1 \right) \times 100$$

ILS values in excess of 50% indicate significant anti-tumor activity, while values in excess of 75% indicate high activity.

TABLE I

Anti-tumor Screening Data (vs. S-180 ascites) For cis-[Pt(NH$_3$)$_2$(OH)]$_2$(H$_2$PO$_4$)$_2$ (Example 1)

| Test No. | Carrier | Dose$^{(a)}$ | Complex of Example 1 % ILS | Survivors | positive Control % ILS$^{(b)}$ | 30-Day Survivors |
|---|---|---|---|---|---|---|
| 1 | Phosphate buffer pH 5$^{(c)}$ | 2.5 | 88 | 5 | 80(8) | 4 |
|   |   | 5 | 100 | 6 |   |   |
|   |   | 10 | 100 | 6 |   |   |
|   |   | 20 | 92 | 5 |   |   |
| 2 | Phosphate buffer | 20 | 100 | 6 | 93(8) | 5 |
|   |   | 40 | −41 | 0 |   |   |
|   |   | 80 | −38 | 0 |   |   |
|   |   | 160 | −83 | 0 |   |   |
| 3 | Phosphate buffer pH 5 | 5 | 63 | 2 | 87(7) | 1 |
|   |   | 10 | 70 | 3 |   |   |
|   |   | 20 | 99 | 5 |   |   |
|   |   | 30 | 100 | 5 |   |   |

| Test No. | Carrier | Dose$^{(a)}$ | Complex of Example 1 % ILS | 30-Day Survivors | Positive Control % ILS$^{(b)}$ | 30-Day Survivors |
|---|---|---|---|---|---|---|
| 4 | Phosphate buffer pH 5 | 5 | 79 | 4 | 54(8) | 1 |
|   |   | 10 | 89 | 4 |   |   |
|   |   | 20 | 88 | 4 |   |   |
|   |   | 30 | −23 | 1 |   |   |
| 5 | H$_2$O | 2.5 | 100 | 6 | 93(8) | 5 |
|   |   | 5 | 87 | 5 |   |   |
|   |   | 10 | −77 | 0 |   |   |
|   |   | 20 | −86 | 0 |   |   |

$^{(a)}$6 mice/dose.
$^{(b)}$7 or 8 mg/kg cis-[Pt (NH$_3$)]Cl$_2$ in saline, amount indicated in parentheses.
$^{(c)}$0.1M sodium phosphate buffer, pH 5.0.

Based on the data set forth in Table I, [Pt(NH$_3$)$_2$(OH)]$_2$-(H$_2$PO$_4$)$_2$ in phosphate buffer (pH=5) showed excellent activity between 2.5 and 20 mg/kg. It was toxic at 40 mg/kg and above. In aqueous solution the compound was also active at 2.5 and 5 mg/kg, but it was strongly toxic at 10 and 20 mg/kg. The phosphate buffer appeared to retard hydrolysis of the complex and thus extended its effective dose upward. The complex had similar threshold doses whether it was in phosphate buffer or in aqueous solution.

For purposes of comparison, anti-tumor screening tests were performed with other cis-diammineplatinum-(II) complexes of the formula cis-$[Pt(NH_3)_2(OH)]_2X_2$ wherein the anion, X, was nitrate, sulfate or perchlorate. The results of these tests are summarized in Table II.

TABLE II

Anti-tumor Screening Data (vs. S-180 ascites) for cis-$[Pt(NH_3)(OH)]_2X_2$; X = $H_2PO_4, NO_3, ClO_4, SO_{4/2}$[a]

| Anion | Test No. | Carrier | Dose[b] | Test Compound % ILS | 30-day Survivors | Positive Control % ILS[c] | 30-Day Survivors |
|---|---|---|---|---|---|---|---|
| $H_2PO_4$ | P-1 | $H_2O$ | 2.5 | 100 | 6 | 93(8) | 5 |
| | | | 5 | 87 | 5 | | |
| | | | 10 | −77 | 0 | | |
| | | | 20 | −86 | 0 | | |
| $NO_3$ | N-1 | $H_2O$ | 4 | 24 | 0 | 82(8) | 1 |
| | | | 8 | 13 | 1 | | |
| | | | 12 | −81 | 0 | | |
| | | | 16 | −100 | 0 | | |
| $SO_4$ | S-1 | $H_2O$ | 2 | 17 | 0 | 68(7) | 1 |
| | | | 3 | 20 | 0 | | |
| | | | 4 | 32 | 0 | | |
| | | | 5 | 37 | 0 | | |
| $ClO_4$ | C-1 | $H_2O$ | 5 | 31 | 1 | 78(8) | 1 |
| | | | 10 | −38 | 0 | | |
| | | | 15 | −68 | 0 | | |

[a]Analyses: $[Pt(NH_3)_2(OH)]_2(NO_3)_2$
Calculated: Pt, 63.30%; H, 2.29%; N, 13.63%; O, 20.77%
Found: Pt, 63.46%; H, 2.25%; N, 13.41%; O, 20.62%
$[Pt(NH_3)_2(OH)]_2(SO_4) \cdot 2H_2O$
Calculated: Pt, 62.48%; H, 2.90%; N, 8.97%; S, 5.13%
Found: Pt, 63.17%; H, 2.65%; N, 9.04%; S, 4.85%
[b]6 mice/dose
[c]7 or 8 mg/kg cis-$[Pt(NH_3)_2]Cl_2$ in saline, amount indicated in parenthesis.

Based on the data set forth in Table II, the perchlorate, nitrate and sulfate salts had no significant anti-tumor activity. In contrast, the dihydrogen phosphate complex showed excellent activity at doses of both 2.5 and 5 mg/kg. The dihydrogen phosphate and perchlorate salts were both toxic at doses of 10 mg/kg. The nitrate salt was toxic at a dose of 12 mg/kg. The toxic dose of the sulfate salt was not reached.

EXAMPLE 5

Evaluation of the Anti-Tumor Activity of the Complex of Example 2 in the S180a System Employing procedures similar to those described in Example 4, the product of Example 2 was tested for anti-tumor activity. The data thus obtained are summarized in Table III.

TABLE III

Anti-Tumor Screening Data (vs. S180 ascites) for Complex of Example 2

| Test No. | Medium | Complex of Example 2 Dose[a] | % ILS | 30-Day Survivors | Positive Control[b] % ILS | 30-Day Survivors |
|---|---|---|---|---|---|---|
| 1 | Klucel- phosphate buffer pH5 slurry[c] | 20 | 37 | 1 | 63 | 1 |
| | | 40 | 89 | 5 | | |
| | | 80 | 88 | 5 | | |
| | | 160 | −20 | 2 | | |
| 2 | Klucel- phosphate | 5 | 53 | 3 | 82 | 3 |
| | | 10 | 91 | 4 | | |

TABLE III-continued

Anti-Tumor Screening Data (vs. S180 ascites) for Complex of Example 2

| Test No. | Medium | Complex of Example 2 Dose[a] | % ILS | 30-Day Survivors | Positive Control[b] % ILS | 30-Day Survivors |
|---|---|---|---|---|---|---|
| | buffer pH5 slurry[c] Day 1,4,8 | 20 | 100 | 6 | | |
| | | 40 | 1 | 2 | | |

[a]6 mice/dose.
[b]Positive Control = 7 mg/kg cis-$[Pt(NH_3)_2Cl_2]$ in saline.
[c]0.1M sodium phosphate buffer, pH 5.0; 0.1–0.3% Klucel.

Based on the data set forth in Table III, the complex of Example 2 showed excellent anti-tumor activity at doses of both 40 and 80 mg/kg on the single dose regimen and at doses of 10 and 20 mg/kg on the divided dose regimen where doses were given on Days 1, 4 and 8. The complex of Example 2 exhibited toxicity at a dose of 160 mg/kg on the single dose regimen and at a dose of 40 mg/kg on the divided dose regimen. The wide effective dose range for this complex may be due to its insolubility (in water), thus in effect providing a slow release of the active agent from a solid reservoir implanted in the peritoneal cavity.

EXAMPLE 6

Evaluation of the Complexes of this Invention in the P388 Tumor System

The complexes of this invention also were screened for activity against the lymphocytic leukemia P388 system in mice, in which the mean survival time as compared with control mice (T/C) was determined. The T/C* is calculated according to the following formula:

$$T/C = \left( \frac{\text{Mean Survival Time (Test)}}{\text{Mean Survival Time (Control)}} \right) \times 100$$

T/C values of at least 125 represent significant activity. The data from these tests are summarized in Table IV.
*T/C is related to %ILS by the following formula: (T/C-100)=%ILS.

TABLE IV

Anti-Tumor Screening Results v. P388 Tumor System

| Complex of Example # | Dose (mg/kg)[a] | T/C | Survivors[c] |
|---|---|---|---|
| 1 | 5 | T[b] | 5/6 |
| | 2.5 | T | 5/6 |
| | 1.25 | 191 | 6/6 |
| | 0.63 | 172 | 6/6 |
| | 0.31 | 130 | 6/6 |
| 1 | 5 | T | 5/6 |
| | 2.5 | 172 | 6/6 |
| | 1.25 | 146 | 6/6 |
| | 0.63 | 117 | 6/6 |
| | 0.31 | 116 | 6/6 |
| 2 | 12.5 | T | 6/6 |
| | 6.25 | 192 | 6/6 |
| | 3.13 | 166 | 6/6 |
| | 1.56 | 141 | 6/6 |
| | 0.78 | 132 | 6/6 |

[a]Dose Regimen: Day 1-9 = Daily doses on days 1 through 9.
[b]T = Toxic according to NCI definitions. (See Geran, et al. Cancer Chemo Rep., Pt. 3, Summer 1972.);
[c]Number of survivors on Day 5.

Based upon the data set forth in Table IV, it can be seen that the yellow cis-$[Pt(NH_3)_2(OH)]_2(H_2PO_4)_2$ Complex of Example 1 possessed maximum activity against P388 at a dose of 1.25 to 2.5 mg/kg on a schedule of 9 daily doses, but was toxic at higher doses.

The gray-blue complex of Example 2 showed maximum activity in the P388 system at a dose of 6.25 mg/kg on a schedule of 9 daily doses, but showed toxicity at higher doses.

What is claimed is:

1. A method for treating malignant S180 ascites or lymphocytic leukemia P388 tumors in a mammal afflicted therewith which comprises administering to said mammal an effective amount of a cis-diammineplatinum(II) orthophosphate complex useful in the treatment of tumors, said complex comprising cis-$\{Pt(NH_3)_2\}$ and an orthophosphate moiety of the formula: $\{(H_{2-n}PO_4)\}^{-(1+n)}$ wherein n is 0 or 1 and the atomic ratio of phosphorous to platinum is about 0.5–1 or about 1—1.

2. A method according to claim 1 wherein said complex has the empirical formula cis-$[Pt(NH_3)_2(OH)]_2(H_2PO_4)_2$.

3. A method according to claim 1 wherein said complex has the empirical formula cis-$\{Pt(NH_3)_2\}_2(HPO_4)(OH_2)(H_2O)$.

4. A method according to claim 1 wherein said complex is hydrated cis-diammineplatinum(II) orthophosphate.